United States Patent [19]

Boulware et al.

[11] Patent Number: 4,818,533

[45] Date of Patent: * Apr. 4, 1989

[54] PRODUCTION OF HIGH PURITY ALKALOIDS

[75] Inventors: Richard T. Boulware, High Point, N.C.; George Schlowsky, Ridgewood, N.J.

[73] Assignee: Vipont Pharmaceutical, Inc., Fort Collins, Colo.

[ * ] Notice: The portion of the term of this patent subsequent to Aug. 30, 2005 has been disclaimed.

[21] Appl. No.: 96,262

[22] Filed: Sep. 4, 1987

Related U.S. Application Data

[63] Continuation of Ser. No. 753,264, Jul. 9, 1985, abandoned, which is a continuation-in-part of Ser. No. 596,589, Apr. 4, 1984, abandoned.

[51] Int. Cl.$^4$ ............. A61K 35/78; A61K 31/44
[52] U.S. Cl. ................. 424/195.1; 514/279; 514/280; 514/282
[58] Field of Search ............. 424/195.1; 514/282, 514/279, 280; 566/61

[56] References Cited

U.S. PATENT DOCUMENTS

| | | | |
|---|---|---|---|
| 3,843,788 | 10/1974 | Iwasa et al. | 424/195.1 |
| 3,849,561 | 11/1974 | Iwasa et al. | 514/284 |
| 4,145,412 | 3/1977 | Landanyi | 424/58 |
| 4,335,110 | 6/1982 | Collins | 424/145 |
| 4,376,115 | 3/1983 | McCrorey | 424/145 |
| 4,406,881 | 9/1983 | Ladanyi | 424/49 |

FOREIGN PATENT DOCUMENTS

| | | |
|---|---|---|
| 2755577 | 6/1979 | Fed. Rep. of Germany . |
| 2856577 | 6/1980 | Fed. Rep. of Germany . |
| 495311 | 4/1976 | U.S.S.R. . |
| 2078109 | 1/1982 | United Kingdom ......... 514/280 |

*Primary Examiner*—John W. Rollins

[57] ABSTRACT

A method for extracting valuable alkaloid materials from plants containing the same comprising slurrying the comminuted plant material in a mixture of water and a cosolvent at a pH of 8.5, adding a nonpolar, water-insoluble, solvent to dissolve the alkaloid, washing the nonpolar phase with acidulated water to convert the alkaloid to the imminium ion or acid salt form, precipitating the alkaloids, and recovering and drying the alkaloid.

10 Claims, 1 Drawing Sheet

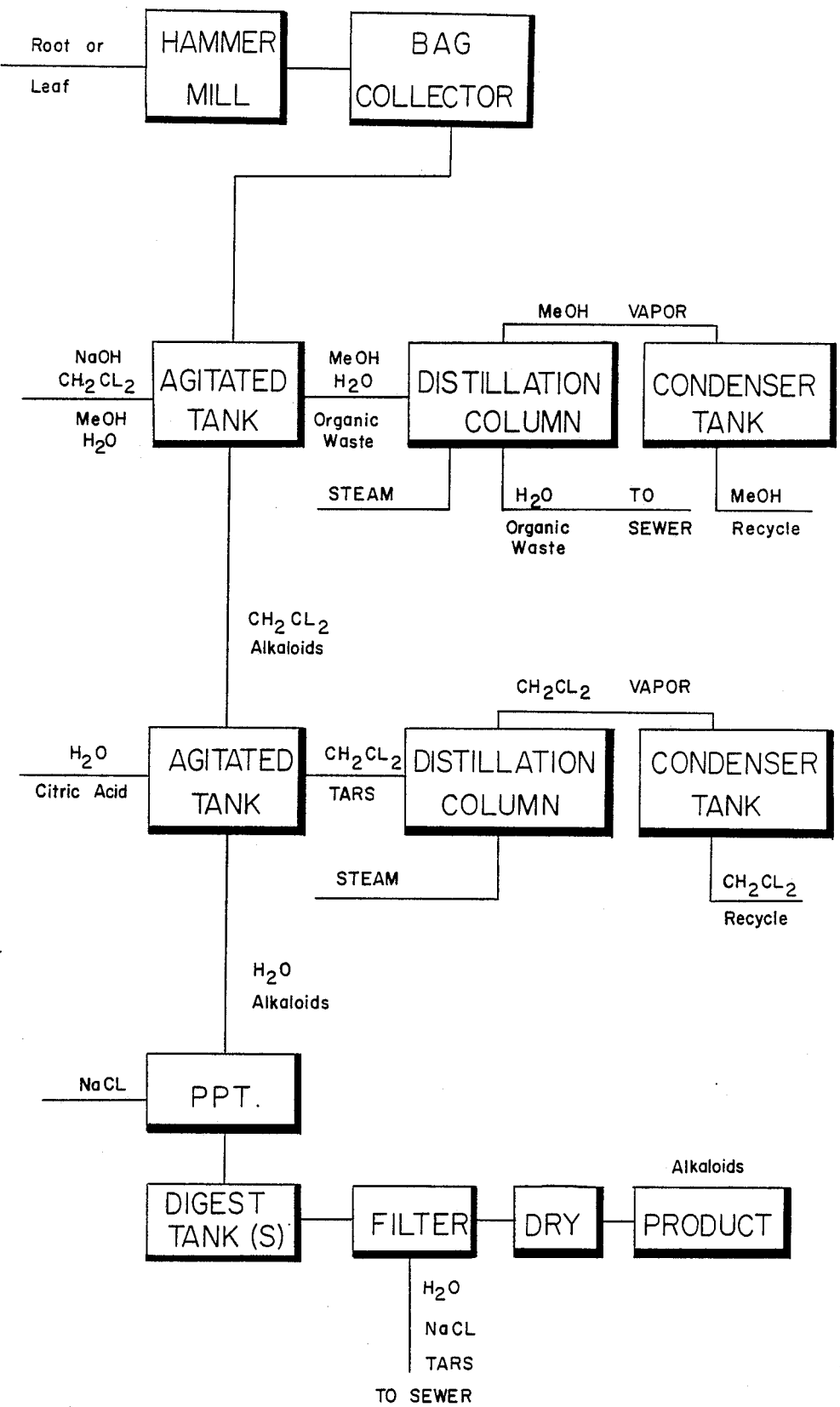

PRODUCTION OF HIGH PURITY ALKALOIDS

This application is a continuation, of application Ser. No. 753,264, filed July 9, 1985, now abandoned, which is a continuation-in-part of Ser. No. 596,589, filed Apr. 4, 1984, now abandoned.

BACKGROUND OF THE INVENTION

This invention relates to a method for recovering active alkaloids which form a free base soluble in non-polar solvent and a water-soluble acid salt, from plants containing these compounds.

Many plants contain valuable alkaloids, which can be used in treating a variety of conditions. Among the uses for plant-derived alkaloids are the chelidonene group, which have been found to be useful against malignant tumors, papillomatosis of the larnyx, and early forms of lupus erythematosus.

Alkaloids of the chelidonene group have so far been found in the fimbriated poppy (*Glaucium fimbrilligerum Boiss.*) and in *Corydalis ledebourania Kar.* et Kir. and *Corydalis severtzovii Regal.* These alkaloids have also been found in the Papaveraceae, such as the species Bocconia (Macleaya) microcarpa (Maxim) Fedde.

*Sanguinaria canadensis, Linn* (family Papvaraceae) is commonly known as bloodroot, redroot, puccoon, teterwort, etc., and is a perennial herb native to North America. The plant and its juices have been used for various purposes in pre-historical and historical times. The plant has been used, in particular, as a folk remedy. The plant has generally been used whole, either undried (fresh) or dried. The usual procedure is to powder the dried plant and mix it with a carrier. This folk remedy has been tried for such conditions as asthma, bronchitis, dysentery, ringworm, and a substantial list of other ailments.

The rhizome of the plant has not been used much in modern times. The present principal use of Sanguinaria is as stimulate expectorant in cough syrups and in homeopathic medicine.

As early patent, U.S. Pat. No. 209,331, disclosers the use of bloodroot, zinc chloride, and Kerosene oil in equal proportions for treating open sores. U.S. Pat. No. 433,257, describes a salve of pulverized bloodroot, armenian bole, powdered rosin, lard, and Stockholm tar for use in the treatment of piles. U.S. Pat. No. 2,344,830, discloses the use of a mixture of zinc chloride, stibnite, and bloodroot to fix and outline diseased tissue for excision by surgery.

More recently, it has been discovered that extracts of sanguinaria and other plants of the families Papaveraceae. Fumariaceae, and Berberidaceae such as *Macleaya cordata, Bocconia frutescens, Corydalis sevctcozii, C. ledebouni, Argemone mexicanus,* and *Chelidonium majus* contain benzo-c-phenanthridine alkaloids which are believed to have valuable properties in conditioning oral tissue, as well as in preventing and treating gingivitis, periodontitis, and mouth odors.

The pure chemical sanguinarine, chelerythrine, protopine, chelerubine, chelilutine, sanguilatine, macarpine, sanguirubine, allocryptopine, homochelidonene, and berberine, can be isolated form plants other than Sanguinaria. They are also available, although rarely, from some chemical supply houses, semi-purified forms of the alkaloids are commercially available, and these are generally referred to as sanguinarine nitrate and sanguinarine sulfate. These "salts" are the salts of the mixed alkaloids of the plant Sanguinaria: namely, sanguinarine, chelerytherine, and protopine. While few references can be found in the literature regarding the usage of any of the pure benzophenanthridine alkaloids, plants containing such compounds have been used for a wide variety of medical ailments.

Several patents have disclosed the use of extracts of Sanguinaria for such purposes, notably U.S. Pat. No. 4,145,412; U.K. Pat. No. 2,042,336; U.S. Pat. No. 4,376,115; U.S. 4,406,881; German Pat. No. 2,907,406; Belgain Pat. No. 888,843. These patents describe the use Sanguinaria extracts as antimicrobial agents as well as mouth treating agents.

The prior art cited above describes a method of extracting active ingredients from Sanguinaria canadensis by extracting cut or ground bloodroot with methanol for at least 24 hours at an elevated temperature, filtering the liquid extract contained, evaporating the extract to dryness, dissolving the dried residue in chloroform, adjusting the chloroform solution to an acid pH by the addition of hydrocloric acid, filtering the acidified extract, evaporating it to dryness, and dissolving the dried residue in glycerine for mixing with a carrier.

V.A. Chelombit'ko et al., in *Khimiko-Farmatsevtiches-kii Zhurnal,* No. 2, 49–52, Feb., 1968, disclose a method of extracting chelerythrine and sanguinarine from plants by soaking the plants in 10% ammonia solution covered with dichloroethane and then in dichloroethane. The solution was alkalified and the alkaloid bases precipitated.

U.S.S.R. Pat. No. 495,311, discloses a method of obtaining greater celandine alkaloids by extracting the leaves of plants containing the alkaloids with aqueous acetone acidified with acetic acid, removing the acetone by distillation, and raising the pH to 10–11 with ammonium hydroxide to precipitate berberine. The precipitate is extracted with trichloromethane to obtain the soluble berberine group alkaloid bases, which can be worked up into berberine, chelidonine hydrochloride, and a mixture of sanguinarine, chelerytherine, and chelilutin.

German Pat. No. 2,856,577 discloses a method of preparing benzophenanthridine alkaloids from plant materials by moistening chopped plant materials with an ammonia solution and subjecting the mixture to a trichloromethane extraction to enrich the alkaloids. Sulfuric acid is added and the solvent is simulataneously distilled off. The residue is basified with ammonia to precipitate the alkaloid free bases which are then filtered off.

SUMMARY OF THE INVENTION

The present invention is directed to a more refined method of obtaining alkaloids form plants of the families Papaveracease, Fumariaceae, and Berberidaceae such as *Sanguinaria canadensis, Macleaya cordata, Macleaya, microcarpa Corydalis sevctvozzii, C. ledebouni, Argemone mexicanus, Chelidonium majus,. Bocconia frutescens,* and mixtures thereof, and other plants which contain alkaloids which form a free base soluble in non-polar solvents and a water soluble acid salt.

The benzo-c-phenanthridine alkaloids which have been identified in Sanguinaria include sanguinarine, chelirubine, sanguirubine, chelilutine, chelerythrine, and sanguilutine.

In the process of the present invention, alkaloid containing plant material is ground and slurried with water or water/solvent mixture. The pH is adjusted to 8.5 with any available base, such as sodium carbonate, ammonium hydroxide, potassium hydroxide, sodium hydroxide, and the like. This converts the alkaloidal constituents to the free base or pseudo base form which may then be extracted in non-polar solvents such as the nonpolar solvent, chloroform, or dichlorethane. It is thus possible to extract the alkaloidal constituents away from more polar, water soluble substances, which remain with the aqueous slurry of ground plant matter.

A phase transfer agent is added to the slurring of ground plant material as a cosolvent for the alkaloids of interest. The phase transfer agent is soluble in both methylene chloride and water, and can be selected from the group consisting of lower ($C_1$–$C_4$) alcohols, lower ($C_1$–$C_4$) ketones, tetrahydrofuran, and dimethyl sulfoxide. The alkaloids of interest for the present process, such as the benzophenanthridines, which are insoluble in water in the pseudobase form, are soluble in the phase transfer agent, which in turn is soluble in the nonpolar solvent as well as water.

One method of processing is for an aqueous slurry of base converted alkaloids to be emulsified with the immisible non-polar phase. This facilitates extraction of the alkaloids into the nonpolar solvent.

The emulsion is broken by filtration. This frees the slurry of ground plant matter and facilitates a phase separation of the aqueous phase from the immiscible non-polar phase. The alkaloids remain with the nonpolar solvent.

The nonpolar phase is washed with acidulated water to convert the alkaloids to the imminium ion or acid salt form. In this form, the alkaloids are water soluble and transfer to the aqueous phase. Nonpolar impurities are retained in the nonpolar phase.

At this point, the alkaloids have passed through two steps which have left polar impurities behind and left nonpolar impurities behind, and the alkaloids exist in a highly refined form. They may at this point be precipitated as acid salts or once again be made basic and extracted back into a nonpolar solvent for the isolation of specific alkaloids.

The alkaloids may be precipitated as the chloride salt with sodium chloride or hydrochloric acid, or as the nitrate or sulfate salt with nitric or sulfuric acid, respectively.

It has been found that recovery of benzophenanthridine alkaloids from bloodroot and *Macleaya cordata* by the process of the present invention is nearly quantitative.

In a preferred embodiment of the invention, the base converted alkaloids are slurried in a nonpolar solvent phase containing sufficient water and cosolvent (phase transfer agent) to effect the extraction of the alkaloids into the nonpolar phase. The nonpolar solvent containing the alkaloids is separated from the ground plant material by filtration.

After filtration, water is added to the nonpolar solvent containing the alkaloids to remove the polar impurities and most of the cosolvent (phase transfer agent) from the non-polar containing alkaloid phase.

Processing then proceeds as above beginning with washing the nonpolar phase with acidulated water.

DETAILED DESCRIPTION OF THE DRAWINGS

The drawing is a block diagram of the process on a commercial scale for extracting alkaloids form plants.

Plant material, generally roots or leaves, is broken up with a hammer mill and collected in a bag collector. The comminuted plant material is optionally recovered in a wet scrubber before being sent to an agitator tank. The comminuted plant material is agitator in a tank with water, methanol and methylene chloride, and caustic, wherein the alkaloids are extracted into the methylene chloride. The methylene chloride containing the alkaloids is directed to an agitated tank where water and citric acid are added to the methylene chloride solution. The two phases are agitated and allowed to reform. The alkaloids are now disolved in the water citric acid phase. The methylene chloride phase is taken to a recovery still and the alkaloids which are dissolved in the water and citric acid phase are precipitated with sodium chloride, digested, and filtered to remove water, excess sodium chloride and soluble tars. The filter cake is dried to obtain the purified alkaloid product.

DETAILED DESCRIPTION OF THE INVENTION

EXAMPLE I

One hundred grams of root from bloodroot, *Sanguinaria canadensis*, were ground or pulverized to a 60/40 mesh and slurried with 500 ml. water, 100 ml methanol, and 2.5 g sodium hydroxide. The pH of the mixture was 8.5.

The slurry was transferred to a 2000 ml separatory funnel and 600 ml methylene chloride were added. The phases were mixed until the methylene chloride turned a deep purple color.

The purple emulsion was broken by passing the liquid through a coarse filter. This filtering step broke the emulsion and removed extraneous ground plant material.

The methylene chloride phase was transferred to a clean 2000 ml separatory funnel and washed with 500 ml of water which contained 15.0 g citric acid. The alkaloids imparted a deep orange color to the water phase.

The water phase was transferred to a clean flask and heated with stirring to 60° C.

Next, 75.0 g sodium chloride (or 10 g/100 ml) is added with stirring at 60° C. and an orange flocculant precipitate was observed to form.

Stirring was discontinued, and the precipitate was allowed to sit for 24 to 48 hours.

The precipitate was collected and dried at 40° C.

The precipitate was about 42% sanguinarine chloride by weight and approximately 80% by weight mixed benzophenanthridine alkaloids. The remaining 20% comprised excess sodium chloride and moisture.

EXAMPLE II

One hundred grams of Macleaya Cordata leaves were ground to a 60/40 mesh and were slurried with 500 ml water, 100 ml methanol, and 2.5 g sodium hydroxide. The pH of the slurry was 8.5.

The slurry was transferred to a 2000 ml separatory funnel and 600 ml methylene chloride was added. The phases were mixed until the methylene chloride became a deep purple.

The slurry, now in the form of a emulsion, was filtered through a coarse filter. This filtering step broke the emulsion and removed extraneous ground plant material.

The methylene chloride phase was transferred to a clean 2000 ml separatory funnel and washed with 500 ml of water which contained 15.0 g citric acid. The alkaloids imparted a deep orange color to the water phase.

The water phase was transferred to a clean flask and heated with stirring to 60° C.

Next, 75.0 ± sodium chloride was added with stirring at 60° C., an an orange precipitate formed.

Stirring was discontinued, and the precipitate was allowed to sit for 24 to 48 hours. The precipitate was collected and dried at 40° C.

The precipitate was about 37% sanguinarine chloride by weight and approximately 80% by weight mixed bentophenanthridine alkaloids. The remaing 20% of the precipitate was excess sodium chloride and moisture.

EXAMPLE III

On hundred grams of ground bloodroot was premixed with 10.0 grams of sodium carbonate and slurried for one hour with a solution of 660 grams methylene chloride, 72 grams isopropyl alcohol, and 28 grams water.

The slurry was then filtered through a coarse filter to remove the plant material and the deep purple extract was transferred to a 2000 ml separatory funnel. The extract was washed twice with 500 ml. neutral water, a total of 1000 ml, to remove water soluble impurities as well as residual isopropyl alcohol. The isopropyl alcohol-water phase was retained, and the isopropyl alcohol was recovered by distillation.

The washed methylene chloride extract was then extracted with 300 ml water containing 9.0 grams citric acid, and then with 200 ml water containing 6.0 grams citric acid. The alkaloids were retained in the acidulated water phase and the methylene chloride phase was retained for distillation and recycling.

The water phase was heated with stirring to 65° C., and 50 grams sodium chloride was added as a precipitating agent. The solution and precipitate were allowed to cool and digest for 24 hous. The precipitate was then collected and dried for 16-24 hours at 40° C.

The precipitate collected was approimately 42% sanguinarine chloride by weight and about 80% by weight mixed benzophenanthridine alkaloids.

EXAMPLE IV

The procedure of Example III was repeated using 100 grams of ground *Macleaya cordata* leaves instead of 100 grams of ground bloodroot leaves.

The precipitate collected was approximately 37% sanguinarine chloride by weight. The total mixed benzophenanthridine alkaloids was about 80% by weight.

What is claimed is:

1. A method for extracting an alkaloid from a plant containing the alkaloid, which alkaloid forms a free base soluble in non-polar solvents and a water soluble acid salt comprising grinding the plant material, slurrying the plant material in a mixture of water and a cosolvent, adjusting the pH of the mixture to a pH of about 8.5, extracting the alkaloid in a nonpolar solvent which is insoluble in water, dissolving the alkaloid into water by lowering the pH of the solution with acid, adding the salt of a mineral acid or a mineral acid to precipitate the alkaloid, and collecting the precipitated alkaloid.

2. The method of claim 1 wherein the nonpolar solvent is selected form the group consisting of methylene chloride, chloroform, and dichloroethane.

3. The method of claim 1 wherein the cosolvent is selected from the group consisting of lower ($C_1$-$C_4$) alcohols, lower ($C_1$-$C_4$) ketones, tetrahydrofuran, and dimethylsulfoxide.

4. The method of claim 1 wherein the pH of the water-cosolvent mixture is raised with a compound selected from the group consisting of sodium carbonate, ammonium hydroxide, potassium hydroxide, and sodium hydroxide.

5. The method of claim 1 wherein the mineral acid is selected form the group consisting of hydrochloric acid, sulfuric acid, and nitric acid.

6. The method of claim 1 wherein the mineral acid salt is sodium chloride.

7. The method of claim 1 wherein the alkaloid is a benzophenanthridine alkaloid.

8. The method of claim 7 wherein the plant is selected from the plant families consisting of Papaveraceae, Fumariaceae, and Berberidaceae.

9. The method of claim 7 wherein the plant is selected from the group consisting of *Sanguinaria canadensis, Macleaya cordata* or *Macleaya microcarpa, Corydalis sevctvozzii, C.ledebouni, Argemine mexicanus, Chelidonium majus, Bocconia frutescens* and mixtures thereof.

10. The method of claim 1 wherein the amount of water used in the mixture of water, and cosolvent, is the minimum amount required to effect extraction of the alkaloids into the nonpolar solvent.

* * * * *